United States Patent [19]

Suciu et al.

[11] Patent Number: 4,479,020

[45] Date of Patent: Oct. 23, 1984

[54] PRODUCTION OF HALOHYDRINS

[75] Inventors: George D. Suciu, Ridgewood; Joon T. Kwon, Freehold Township, Monmouth County; Atef M. Shaban, Nutley, all of N.J.

[73] Assignee: The Lummus Company, Bloomfield, N.J.

[21] Appl. No.: 440,952

[22] Filed: Nov. 12, 1982

[51] Int. Cl.³ .................... C07C 31/34; C07C 31/36
[52] U.S. Cl. .................................. 568/850; 568/812; 568/821; 568/822; 568/838
[58] Field of Search ............... 568/850, 812, 822, 838, 568/839, 821

[56] References Cited

U.S. PATENT DOCUMENTS

| | | | |
|---|---|---|---|
| 1,315,229 | 9/1919 | McElroy | 568/850 |
| 2,315,557 | 4/1943 | Soday | 568/812 |
| 4,008,133 | 2/1977 | Gelbein | 549/521 |
| 4,277,405 | 7/1981 | Apanel | 568/840 |

*Primary Examiner*—Howard T. Mars
*Attorney, Agent, or Firm*—Elliot M. Olstein; John N. Bain

[57] ABSTRACT

Production of halohydrins; in particular, chlorohydrins by reaction of tertiary alkyl hypohalite and olefinically unsaturated compound in the presence of water and a metal selected from Group II-A, II-B, III-A, III-B, IV-A, IV-B, or V-A of the Periodic Table. The use of such metals improves the production of halohydrin.

17 Claims, No Drawings

PRODUCTION OF HALOHYDRINS

This invention relates to the production of halohydrins, and more particularly to the production of chlorohydrins.

U.S. Pat. No. 4,008,133 is directed to the production of epoxy compounds from olefinic compounds, and in such a process, a halohydrin, and in particular, a chlorohydrin is produced by reaction of olefinically unsaturated compound with tertiary alkyl hypochlorite in the presence of water, with the chlorohydrin then being saponified to the olefin oxide.

The present invention is directed to providing a more efficient process for the production of a halohydrin, and in particular a chlorohydrin.

In accordance with the present invention, there is provided a process for producing a halohydrin, and in particular, a chlorohydrin, by reaction of an olefinically unsaturated compound with a tertiary alkyl hypohalite, and in particular, a tertiary alkyl hypochlorite, in the presence of water, wherein the improvement resides in producing the halohydrin in the presence of at least one metal selected from Group II-A, II-B, III-A, III-B, IV-A, IV-B or V-A of the Periodic Table (mendeleef Periodic Table).

Applicant has found that the use of such metals, and in particular, magnesium, zinc, aluminum and tin, improves the production of the desired halohydrin.

Although the present invention has broad applicability to the production of halohydrins, the present invention has particular applicability to the production of a chlorohydrin by reaction of a tertiary alkyl hypochlorite with an olefinically unsaturated compound.

The metal is employed in solid form, and may be in any one of a wide variety of shapes, such as powders, granules, pellets, thin sheets, etc., and may be employed in either a supported or unsupported form. Similarly, the metal can be deposited on the walls of the reaction vessel.

The metal is employed in the reaction system in a manner such that there is effective contact between the metal and liquid phases. The metal is employed in an amount effective to improve production of the desired chlorohydrin. In general, the dispersed metal can be employed in an amount as low as 1-10 g per 100 ml of liquid reaction mixture, which can be expressed as 1-10 cm² of macroscopic metal surface per 100 ml of reaction mixture. It is to be understood, however, that in some cases lower amounts may be employed. Similarly, higher amounts could be employed without adversely affecting selectivity.

The reaction between the olefinically unsaturated compound, tertiary alkyl hypochlorite, and preferably tertiary butyl hypochlorite, in the presence of water, and the noted metal is preferably conducted at a temperature of from 15° to 85° C., and more preferably, at a temperature of from 40° to 70° C. The upper temperature is set by the decomposition of the hypohalite, and it is to be understood, in some cases, higher or lower temperatures can be employed. The reaction pressure may be atmospheric, superatmospheric or subatmospheric pressure, with a preferred pressure generally being in the order of from 5 to 40 psig.

In the reaction, in general, the water to organic volume ratio is at least 0.1 to 1 and preferably at least 1 to 1. In most cases, the water to organic volume ratio does not exceed 10 to 1; however, higher amounts may be employed.

With respect to the hypochlorite to olefin ratio, it is advantageous the olefin be in a slight stoichiometric excess. In this manner, a complete conversion of the hypochlorite is achieved and the formation of undesired byproduct is minimized. It has been found that use of the olefin in an amount of 2-10% in excess of the stoichiometric amount (expressed as moles) is sufficient for achieving complete conversion of hypochlorite.

The reaction system is comprised of one or more fluid phases, as well as the solid metal phase. The fluid phase may be comprised of a liquid phase or a gaseous phase and a liquid phase, with the liquid phase being either one or two phases. Thus, for example, there may be a separate aqueous and organic phase. As hereinabove noted, however, there is always a solid phase present in the system, with such solid phase being comprised of a metal as hereinabove described.

The reaction may be accomplished in either a batch, semi-batch or continuous reaction system, with the choice of a specific system being deemed to be within the scope of those skilled in the art from the teachings herein.

The production of chlorohydrin from olefinically unsaturated compound, hypochlorite and water, as disclosed in U.S. Pat. No. 4,008,133 is preferably effected with a feed which does not contain a chloride ion concentration in excess of 1 mole per liter and preferably the chloride ion concentration should not exceed 0.1 mole per liter.

In general, in employing tertiary alkyl hypochlorite as one of the reactants in the production of the chlorohydrin, when such hypochlorite has been produced by reaction of chlorine, base and tertiary alkanol, such tertiary alkyl hypochlorite may include some amounts of free chlorine, and such amounts should be maintained as low as possible in order not to generate high amounts of additionally chlorinated byproduct. As disclosed in U.S. Pat. No. 4,008,133, it is preferred to limit the amount of free chlorine so that it does not exceed about 7 moles of chlorine per 100 moles of hypochlorite. It is to be understood that greater amounts of chlorine could be present, but such greater amounts may reduce the yield of desired chlorohydrin.

The chlorohydrin production, in the presence of a metal, as hereinabove described, may be conducted in the presence of an inert organic solvent, as disclosed in U.S. application Ser. No. 35,558, filed on May 3, 1979. As disclosed in such application, the presence of the organic solvent facilitates subsequent separation of the chlorohydrin product, and tertiary alkanol byproduct into an organic phase, which can be subsequently separated from an aqueous phase. As representative examples of such inert organic solvent, there may be mentioned chlorinated hydrocarbons such as chlorinated aromatics; e.g., o-dichlorobenzene; chlorinated paraffin such as carbon tetrachloride, chloroform, dichloropropane, etc.; ketones; e.g., methyl ethyl ketone, methyl isobutyl ketone, acetone, and the like. The solvents may be employed alone or as a mixture of two or more thereof.

Thus, in accordance with the present invention, chlorohydrin is produced from olefinically unsaturated compound, tertiary alkyl hypochlorite and water, in the presence or absence of an inert organic solvent, and in the presence of a metal, as hereinabove described, in order to improve selectivity.

The olefinically unsaturated compound employed as feed in the present process may be any one of a wide variety of olefinically unsaturated compounds, including both mono-olefinically and di-olefinically unsaturated compounds. The olefinically unsaturated compounds generally employed as feed are represented by the following structural formula:

wherein $R_1$ and $R_2$ are each separately either hydrogen; alkyl; halo, naphthyl, and phenyl substituted alkyl; phenyl; halo and alkyl substituted phenyl; naphthyl; halo and alkyl substituted naphthyl; alkenyl; halo substituted alkenyl; and $R_1$ and $R_2$ can be linked together to provide a cycloalkene (generally 5 to 10 carbon atoms). The alkyl and alkenyl groups generally have 1 to 6 carbon atoms and the halo group is preferably iodo-, bromo-, chloro-, most preferably chloro-. As representative examples of the most suitable feedstocks, there may be mentioned; alkenes having from 2 to 6 carbon atoms, preferably 2 to 4 carbon atoms with ethylene and propylene being particularly preferred; styrene; stilbene; butadiene; chloroprene; allyl chloride; allyl bromide; bromoprene; cyclohexene, and cyclopentene. The chlorohydrin produced in accordance with the invention are represented by the following structural formula:

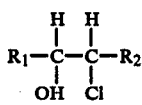

wherein $R_1$ and $R_2$ are as defined above.

The present invention for producing a chlorohydrin has particular applicability to an overall process for producing olefin oxide wherein tertiary butyl hypochlorite, amyl hypochlorite, preferably tertiary butyl hypochlorite, is produced by reaction between tertiary alkanol, chlorine and aqueous base, with the tertiary alkyl hypochlorite then being reacted with olefinically unsaturated compound and water, in the presence of catalyst, as hereinabove described, to produce chlorohydrin and tertiary alkanol byproduct. The chlorohydrin is saponified to the olefin oxide, and the tertiary alkanol byproduct from the chlorohydrin production step is recycled to the hypochlorite production. Such a process is described, for example, in U.S. Pat. No. 4,008,133, with the present invention providing an improvement in such process by increasing the selectivity of chlorohydrin.

The present invention is also applicable to various modifications of the basic process for producing olefin oxide, as described in U.S. application Ser. Nos. 35,557, 35,558, and 35,560, all filed on May 3, 1979.

The invention will be further described with respect to the following examples; however, the scope of the invention is not to be limited thereby.

EXAMPLE 1

A stainless steel autoclave provided with stirring, inlet/outlet ports, pressure gauge and temperature control is used. One hundred grams of water and 8.5 grams (110 mili moles) of allyl chloride are introduced into the autoclave together with one gram of aluminum granules (8–20 mesh). The contents of the autoclave is stirred and brought up to the reaction temperature. Pure t-butyl-hypochlorite (t-BuOCl) is pumped with a constant flow rate of approximately 1 ml/min into the autclave for approximately 12 minutes. A total of 96 mili moles of t-BuOCl was used. The reaction temperature was 75° C., the pressure was 24 psig. The stirring was continued for an additional five minutes after the flow of t-BuOCl was discontinued. The autoclave was then cooled to 15° C., opened and its content was analyzed. The conversion of t-BuOCl was complete.

Analysis of the products indicates that the selectivities (expressed as moles of product formed per 100 moles t-BuOCl reacted) of the various products were: Glycerol dichlorohydrin (DCH) 95.6%, 1,1,1 Trichloropropane (TCP) 2.0%, various ethers, etc. (ETH) 2.4%.

The concentrations of the aluminum dissolved in the organic and aqueous phases was <1 ppm and 12 ppm, respectively.

EXAMPLE 2

The reaction described in Example 1 was repeated. Zinc powder (1.0 g) was used instead of the aluminum. The following selectivities were obtained: DCH 85.9%, TCP 2.7%, ERH 11.4%.

EXAMPLE 3

The reaction described in Example 1 was repeated. Turnings of magnesium (1.0 g) were used instead of the aluminum. The following selectivities were obtained: DCH 94.7%, TCP 1.0%, ETH 4.3%.

EXAMPLE 4

The reaction described in Example 1 was repeated. Chips of tin (1.0 g) were used instead of the aluminum. The following selectivities were obtained: DCH 92.1%, TCP 2.2%, ETH 5.7%.

EXAMPLE 5

Two autoclaves identical to the one used in Example 1 are connected in series so that the liquid mixture from the first enters the second one. The first autoclave is fed via two metering pumps with allyl chloride and t-BuOCl from two feed vessels. The second vessel is connected via a back-pressure regulator to a decanter. The liquid effluent separates here in two phases. The aqueous phase is continuously recycled to the first vessel by means of a metering pump. The organic effluent is removed periodically from the decanter and analyzed.

In each of the autoclaves were introduced 10 g of aluminum granules (8–20 mesh) and 100 ml of water. In the decanter also were introduced 100 ml $H_2O$.

After the contents of the reactors have been heated to 70°–75° C. under stirring, the flows of allyl chloride (0.9 ml/min) and t-BuOCl (1.0 ml/min) are started. The water phase from the decanter is recycled to the first reactor at a rate of 12 ml/min. the back-pressure regulator is set at 24 psig.

After the system has reached equilibrium, a sample of the organic phase removed from the decanter is analyzed. The following selectivities were obtained: DCH 88.5%, TCP 3.1%, ETH 8.0%.

EXAMPLE 6

The reaction system described in Example 5 is modified in the sense that the inlet line for allyl chloride is disconnected and replaced with one through which compressed propylene may be fed to the first reactor. A branching in the line provides propylene to the second reactor also.

In each reactor, 10 grams of aluminum granules and 100 ml of water are introduced. The system is flushed with propylene and then pressurized with same to 50 psig. Stirring is started and temperature is brought up to 70° C. The vessel which was used in Example 5 as decanter is now disconnected from the exit of the second reactor and is used as a feed tank for fresh water. A receiving tank is connected to the exit of the second reactor.

A solution of t-BuOCl in an equal volume of t-BuOH is fed to the first reactor with a flow rate of 2.4 ml/min, at the same time with 4.4 ml/min water. The effluent from the second reactor is collected and analyzed. The following selectivities were obtained: Propylene chlorohydrin 82.8%, dichloropropane 4.8%, ethers 7.9%, other products 4.5%.

The present invention is particularly advantageous in that it is possible to increase the production to desired chlorohydrin, while maintaining or improving selectivity.

Numerous modifications and variations of the present invention are possible in light of the above teachings and, therefore, within the scope of the appended claims, the invention may be practiced otherwise than as particularly described.

What is claimed is:

1. A process for producing halohydrin, comprising: reacting an olefinically unsaturated compound with a tertiary alkyl hypohalite in the presence of water and at least one metal selected from the Group consisting of II-A, II-B, III-A, III-B, IV-A, IV-B and V-A metals of the Periodic Table in an amount effective to increase production of halohydrin.

2. The process of claim 1 wherein the hypohalite is a hypochlorite.

3. The process of claim 2 wherein the metal is selected from the group consisting of magnesium, zinc, aluminum and tin.

4. The process of claim 3 wherein the olefin is allyl chloride.

5. The process of claim 3 wherein the metal is magnesium.

6. The process of claim 3 wherein the metal is zinc.

7. The process of claim 3 wherein the metal is aluminum.

8. The process of claim 3 wherein the metal is tin.

9. The process of claim 3 wherein the metal is employed in an amount of from 1 to 10 grams per 100 ml of liquid reaction mixture.

10. The process of claim 9 wherein the olefin is allyl chloride.

11. The process of claim 10 wherein the temperature of reaction is from 15° to 85° C.

12. The process of claim 11 wherein the water to organic volume ratio is at least 1:1 and does not exceed 10:1.

13. The process of claim 12 wherein the olefin is employed in an amount of from 2% to 10% in excess of the stoichiometric amount, expressed as moles.

14. The process of claim 13 wherein the metal is magnesium.

15. The process of claim 13 wherein the metal is zinc.

16. The process of claim 13 wherein the metal is aluminum.

17. The process of claim 13 wherein the metal is tin.

* * * * *